United States Patent
Linder et al.

(10) Patent No.: US 9,952,184 B2
(45) Date of Patent: Apr. 24, 2018

(54) ULTRASONIC MONITORING OF ELECTRICAL CONNECTIONS

(71) Applicant: SCHNEIDER ELECTRIC IT CORPORATION, West Kingston, RI (US)

(72) Inventors: Stephen Paul Linder, Medford, MA (US); Bret Alan Orner, Arlington, MA (US); David E. Reilly, Concord, MA (US); Jeffrey Stephen Young, Tewksbury, MA (US)

(73) Assignee: SCHNEIDER ELECTRIC IT CORPORATION, West Kingston, RI (US)

( * ) Notice: Subject to any disclaimer, the term of this patent is extended or adjusted under 35 U.S.C. 154(b) by 140 days.

(21) Appl. No.: 14/973,007

(22) Filed: Dec. 17, 2015

(65) Prior Publication Data

US 2017/0176394 A1 Jun. 22, 2017

(51) Int. Cl.
*G01N 29/07* (2006.01)
*G01N 29/34* (2006.01)

(52) U.S. Cl.
CPC ........... *G01N 29/07* (2013.01); *G01N 29/343* (2013.01); *G01N 2291/102* (2013.01); *G01N 2291/2698* (2013.01)

(58) Field of Classification Search
CPC ............. G01N 29/07; G01N 2291/011; G01R 31/045; G01R 31/043; G01R 31/041
USPC .................................................. 73/597, 598
See application file for complete search history.

(56) References Cited

U.S. PATENT DOCUMENTS

| | | |
|---|---|---|
| 7,411,403 B2 | 8/2008 | Zhou |
| 9,057,752 B2 | 6/2015 | Luebke et al. |
| 9,127,998 B1 | 9/2015 | Guldiken et al. |

FOREIGN PATENT DOCUMENTS

WO 2014043082 A1 3/2014

OTHER PUBLICATIONS

Extended European Search Report from corresponding European Application No. 16202529.0 dated Apr. 25, 2017.
Volker Deutsch et al., "Ultraschallprufverfahren" In: "Ultraschallpruefung: Grundlagen und Industrielle Anwendungen", Jan. 1, 1997 (Jan. 1, 1997), Springer Verlag Berlin, New York Heidelberg, XP055363953, ISBN: 978-3-540-62072-3; pp. 74-81.
Braunovic, M. et al., "Part 1—Fundamentals of Electrical Contacts", 2006 by Taylor & Francis Group, LLC, pp. 659.
Newport, Ron, (Feb. 1998), The Loose Electrical Connection Myth, Retrieved from URL: http://www.maintenancetechnology.com/1998/02/the-loose-electrical-connection-myth/.
Product Catalog, 2014 imaging1.com, Retrieved from URL: http://www.imaging1.com/handheld-FLIR-infrared-camera.html.
(Continued)

*Primary Examiner* — Peter Macchiarolo
*Assistant Examiner* — Anthony W Megna Fuentes
(74) *Attorney, Agent, or Firm* — Lando & Anastasi, LLP

(57) ABSTRACT

According to one aspect, embodiments herein provide an electrical connection sensor comprising at least one transducer configured to be coupled to a power distribution block, to generate ultrasonic pulses in the power distribution block, and to receive ultrasonic signals based on the ultrasonic pulses, and a controller coupled to the at least one transducer and configured to determine a status of at least one electrical connection in the power distribution block based on at least one characteristic of the ultrasonic signals received by the at least one transducer.

18 Claims, 3 Drawing Sheets

(56) References Cited

OTHER PUBLICATIONS

Texas Instruments Data Sheet, TDC1000 Ultrasonic Sensing Analog Front End (AFE) for Level Sensing, Flow Sensing, Concentration Sensing, and Proximity Sensing Applications, SNAS648B—Oct. 2014—Revised Aug. 2015, pp. 60.
Texas Instruments User's Guide, TDC100-TDC7200EVM User's Guide, SNIU021A—Oct. 2014—Revised Nov. 2015, pp. 49.
Texas Instruments website, Retrieved from URL: http://www.ti.com/tool/tdc1000-tdc7200evm.

ULTRASONIC MONITORING OF ELECTRICAL CONNECTIONS

BACKGROUND OF INVENTION

Field of the Invention

At least one example in accordance with the present invention relates generally to the monitoring of electrical connections.

Discussion of Related Art

Electronic systems, such as uninterruptible power supplies, generally include power distribution blocks to facilitate connection between two groups of wires. Such power distribution blocks typically use set screws to capture wires inserted in the power distribution block. For example, in a common power distribution block, a first wire is inserted into an opening of the power distribution block and is located adjacent a contact surface. The contact surface is electrically coupled to a terminal. As a user tightens a set screw of the power distribution block, the set screw (or a corresponding stud) moves downward, compressing the first wire against the contact surface and electrically coupling the first wire to the terminal. One or more additional wires can be inserted into additional receptacles of the power distribution block to electrically couple the additional wire(s) to the first wire.

SUMMARY

Aspects in accord with the present invention are directed to an electrical connection sensor comprising at least one transducer configured to be coupled to a power distribution block, to generate ultrasonic pulses in the power distribution block, and to receive ultrasonic signals based on the ultrasonic pulses, and a controller coupled to the at least one transducer and configured to determine a status of at least one electrical connection in the power distribution block based on at least one characteristic of the ultrasonic signals received by the at least one transducer.

According to one embodiment, the ultrasonic signals received by the at least one transducer include a series of reflections from the at least one electrical connection in the power distribution block, and in determining the status of the at least one electrical connection, the controller is further configured to determine a round trip time of at least one of the series of reflections and determine the status of the at least one electrical connection based on the round trip time of the at least one of the series of reflections. In one embodiment, in determining the round trip time of the at least one of the series of reflections, the controller is further configured to determine a round trip time of a most prominent reflection in the series of reflections. In another embodiment, in determining the status of the at least one electrical connection, the controller is further configured to analyze the round trip time of the most prominent reflection in the series of reflections over time and determine the status of the at least one electrical connection based on variations in the round trip time of the most prominent reflection in the series of reflections.

According to another embodiment, in determining the status of the at least one electrical connection, the controller is further configured to identify that the at least one electrical connection has loosened or been overtightened in response to determining that the round trip time of the most prominent reflection in the series of reflections has increased. In one embodiment, the controller is further configured to provide an indication to an external system that the at least one electrical connection has loosened or been overtightened.

According to one embodiment, in determining the round trip time of the at least one of the series of reflections, the controller is further configured to determine the round trip time of at least one secondary reflection in the series of reflections, and in determining the status of the at least one electrical connection, the controller is further configured to determine the status of the at least one electrical connection based on the most prominent reflection and the at least one secondary reflection in the series of reflections. In one embodiment, in determining the status of the at least one electrical connection based on the most prominent reflection and the at least one secondary reflection in the series of reflections, the controller is further configured to identify a torque characteristic of the at least one connection based on the most prominent reflection and the at least one secondary reflection in the series of reflections.

According to another embodiment, the at least one transducer is further configured to receive the series of reflections from a first electrical connection and a second electrical connection in the power distribution block, and the controller is further configured to determine a status of the first electrical connection and a status of the second electrical connection based on the round-trip time of the at least one of the series of reflections. In one embodiment, the at least one transducer includes a first transducer configured to receive a first series of reflections from the first electrical connection and a second transducer configured to receive a second series of reflections from the second electrical connection, and the controller is further configured to determine a first round-trip time of the first series of reflections, to determine a second round-trip time of the second series of reflections, to determine a status of the first electrical connection based on the first round-trip time, and to determine a status of the second electrical connection based on the second round-trip time.

According to one embodiment, the at least one transducer includes a first transducer configured to generate the ultrasonic pulses in the power distribution block and monitor the series of reflections received from the at least one electrical connection in the power distribution block and at least one second transducer configured to monitor the ultrasonic pulses generated by the first transducer, and the controller is further configured to determine the round-trip time of at least one of the series of reflections based on series of reflections monitored by the first transducer and the ultrasonic pulsed monitored by the at least one second transducer. In one embodiment, the at least one transducer is configured to be coupled to the power distribution block with one of an adhesive, a magnet, and a fastener. In another embodiment, the at least one transducer is configured to be coupled to one of a portion of the power distribution block that is orthogonal to a set screw of the at least one electrical connection and a portion of the power distribution block that is in line with a set screw of the at least one electrical connection. In one embodiment, the controller is an analog front end controller.

Another aspect in accord with the present invention is directed to a method for monitoring at least one electrical connection in a power distribution block, the method comprising generating, with at least one transducer, ultrasonic pulses in the power distribution block, receiving, with the at least one transducer, ultrasonic signals based on the ultrasonic pulses, and determining, with a controller coupled to the at least one transducer, a status of at least one electrical connection in the power distribution block based on at least one characteristic of the ultrasonic signals received by the at least one transducer.

According to one embodiment, receiving the ultrasonic signals includes receiving, with the at least one transducer, a series of reflections from the at least one electrical connection in the power distribution block and determining the status of the at least one electrical connection includes determining a round-trip time of at least one of the series of reflections and identifying whether the at least one electrical connection in the power distribution block has loosened or been overtightened based on the round-trip time of the at least one of the series of reflections. In one embodiment, determining the round-trip time of the at least one of the series of reflections includes determining a round-trip time of a most prominent reflection in the series of reflections, and identifying includes analyzing the round-trip time of the most prominent reflection in the series of reflections over time and identifying that the at least one electrical connection in the power distribution block has loosened or been overtightened in response to a determination that the round-trip time of the most prominent reflection in the series of reflections has increased.

According to another embodiment, the method further comprises, in response to identifying that the at least one electrical connection has loosened or been overtightened, providing an indication to a user that the at least one electrical connection in the terminal has loosened or been overtightened. In one embodiment, the method further comprises analyzing at least one secondary reflection in the series of reflections, and determining a torque characteristic of the at least one electrical connection based on the most prominent reflection and the at least one secondary reflection.

At least one aspect in accord with the present invention is directed to a power distribution block comprising a housing, at least one terminal in the housing that is configured to be coupled to a wire, at least one transducer coupled to the housing and configured to generate ultrasonic pulses in the power distribution block and receive ultrasonic signals based on the ultrasonic pulses, and a controller coupled to the at least one transducer and configured to determine a status of a connection between the wire and the at least one terminal based on at least one characteristic of the ultrasonic signals received by the at least one transducer.

BRIEF DESCRIPTION OF DRAWINGS

The accompanying drawings are not intended to be drawn to scale. In the drawings, each identical or nearly identical component that is illustrated in various FIGS. is represented by a like numeral. For purposes of clarity, not every component may be labeled in every drawing. In the drawings.

DETAILED DESCRIPTION

Figure 1:
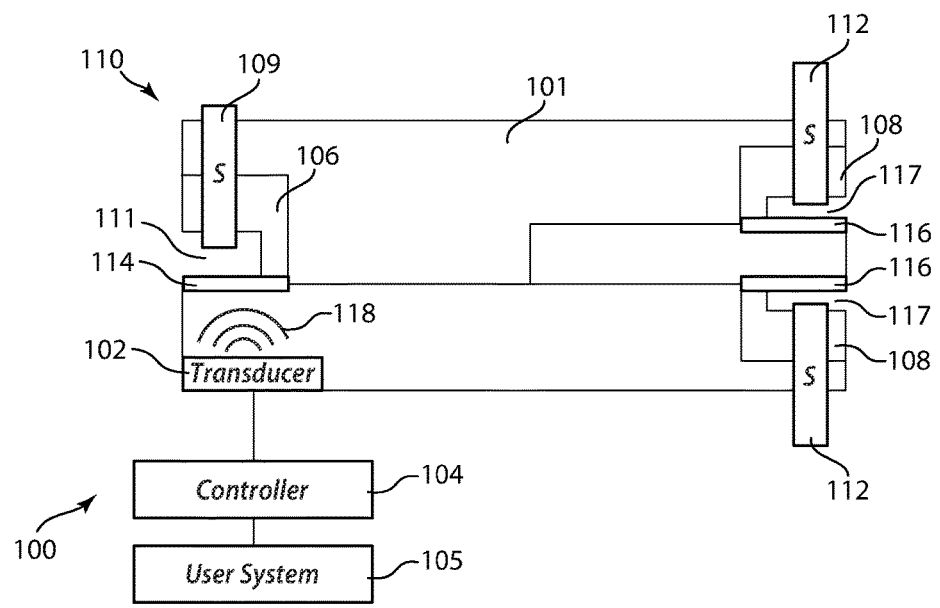
FIG. 1 is a block diagram of an electrical connection sensor in accordance with aspects of the present invention.

Examples of the methods and systems discussed herein are not limited in application to the details of construction and the arrangement of components set forth in the following description or illustrated in the accompanying drawings. The methods and systems are capable of implementation in other embodiments and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated references is supplementary to that of this document; for irreconcilable inconsistencies, the term usage in this document controls.

As discussed above, power distribution blocks are commonly used to facilitate connection between two groups of wires and typically use set screws to capture wires inserted in the power distribution block. Over time, power distribution block connections can loosen either from a set screw unscrewing (e.g., due to thermal cycling) or from deformation of cable material. If a connection loosens sufficiently to cause an increase in resistance through the connection when electrical current passes through the connection, the increase in electrical resistance can cause significant heating of the connection that results in a fire, catastrophic failure, and/or calibration issues during a manufacturing process.

More specifically, the heating of a connection may cause thermal expansion which results in contact surfaces of the connection being exposed to oxygen. The exposure to oxygen may result in corrosion of the connection. The thermal expansion and/or corrosion of the connection may result in a positive feedback loop that leads to the resistance of the connection increasing further. This may result in thermal runaway and pose a fire hazard. Additionally, if a connection has loosened to the point where the resistance has increased enough to cause resistive heating, there is a chance that oxidation of the connection has already occurred. If the connection has had a chance to oxidize, a simple tightening of the connection will no longer be sufficient to restore a proper electrical connection. Instead the connection must be undone, cleaned, and then re-torqued to restore the connection to a low resistance state. Over-tightening of the connection (e.g., of the set screw) will not resolve the problem and may also cause the connection to fail by deforming the set screw and/or cable past its elastic limit. Accordingly, it is important to detect a loose connection early before resistive heating can occur and cause corrosion.

Typically, active connections are not periodically tested mechanically due to the potentially high voltage in the connection, and arc flash concerns. A common approach for monitoring an active electrical connection involves using an Infrared (IR) camera to provide a temperature measurement of the connection without making physical contact. Utilizing this method, testing is performed on energized equipment while current passes through the connection. The IR testing requires a trained person to visit the connection panel and to disable or remove safety features of the system to allow access for the infrared sensor. During the test period, safety precautions, including possibly the use of PPE (Personal Protective Equipment), may be required to test the electrical connection using the IR sensor.

IR testing can be inefficient, expensive, and may provide inaccurate results. For example, current standards require that thermal imaging be periodically performed several times a year on live electrical equipment at a significant cost to the end user of the equipment. For multiple connections having loads with similar current ratings, any connection that shows a higher temperature than others is typically considered faulty. This approach can provide erroneous results depending on the actual current being drawn by each of the loads at the time of the testing. A faulty connection through which no current is passing at the time of the test will not be detected as faulty, and a connection through which a relatively high current is passing at the time of test may be suspected as being faulty.

Additionally, a mechanically loose or over-torqued electrical connection may have a very small resistance and could be difficult to detect with a thermal imaging camera. For example, a 10μΩ increase in resistance when a set screw on a power distribution block is loosened results in a power dissipation of 0.2 W with a 100 A load and of 0.008 W with a 20 A load. Such low power dissipations are difficult, if not impossible, to detect with a thermal imaging camera and a connection having such a small increase in resistance would appear to be functioning correctly, even though the connection is not mechanically robust and could easily worsen.

A more efficient, cost-effective, and accurate sensor for the monitoring of the mechanical state of an electrical connection is provided. In at least one embodiment, the sensor uses an ultrasonic signal to continuously evaluate the mechanical integrity of at least one electrical connection. More specifically, the sensor monitors the mechanical interface between set screw, cable, and housing using ultrasonic pulses. The sensor analyzes one or more characteristics (e.g., round trip time, intensity, shape, etc.) of resulting reflections to determine the state of at least one electrical connection. For example, in at least one embodiment, an analog electronic front end measures the time of flight of the ultrasonic pulses and analyzes the resulting data to ascertain mechanical properties of electrical connections.

FIG. 1 is a block diagram of one embodiment of an electrical connection sensor 100 in accordance with aspects described herein. The electrical connection sensor 100 includes a transducer 102 and a controller 104 coupled to the transducer 102. The transducer 102 is configured to be coupled to a power distribution block 110. The power distribution block 110 includes a housing 101, a terminal 106 located in the housing 101, and at least one terminal 108 located in the housing 101. The terminal 106 includes a corresponding set screw 109 and a cavity 111. Each terminal 108 also includes a corresponding set screw 112 and a cavity 117. As shown in FIG. 1, the power distribution block 110 includes a single terminal 106 and two terminals 108; however, in other embodiments, the power distribution block 110 may include any number of terminals 106 and/or any number of terminals 108.

The terminal 106 includes a contact surface 114 within the cavity 111 and each terminal 108 includes a contact surface 116 within the cavity 117. The contact surface 114 of the terminal 106 is electrically coupled to the contact surface 116 of each terminal 108. The cavity 111 of the terminal 106 is configured to receive a wire. Once a wire is inserted into the cavity 111, a user can tighten the set screw 109 to compress the wire against the contact surface 114. The cavity 117 of each terminal 108 is configured to receive a wire. Once a wire is inserted into a cavity 117, a user can tighten a corresponding set screw 112 to compress the wire against the corresponding contact surface 116. When a wire is coupled to the terminal 106 (i.e., compressed against the contact surface 114) and a wire is coupled to the terminal 108 (i.e., compressed against the contact surface 116), the wire in the terminal 106 is electrically coupled to the wire in the terminal 108.

In one embodiment, the transducer 102 is attached to the housing 101 of the power distribution block 110, adjacent the terminal 106, with magnets, a fastener, an adhesive, etc. In at least one embodiment, the transducer 102 is removable from the power distribution block 110. However, in at least one embodiment, the transducer 102 is permanently embedded in the housing 101 of the power distribution block 110.

According to at least one embodiment, the electrical connection sensor 100 is configured to monitor the electrical connection of a wire to the terminal 106. For example, once a wire is coupled to the terminal 106, as described above, the transducer 102 generates ultrasonic pulses in the power distribution block 110. The ultrasonic pulses reflect off of the boundaries and interfaces of the power distribution block 110 and these reflections are received by the transducer 102. For example, the mechanical geometry of the power distribution block 110, the rigidity of the power distribution block 110, and the interfaces between the inserted wire, the terminal 106, the contact surface 114, and the set screw 109, determine how reflections are provided back to the transducer 102 in response to the ultrasonic pulses generated by the transducer 102. Because of the multiple possible paths that can be taken by the ultrasonic pulses and the resulting reflections, the transducer 102 receives a series of reflections.

The controller 104 analyzes one or more characteristics of the reflections received by the transducer to evaluate the mechanical integrity of the connection (i.e., at the terminal 106) of the power distribution block 110. More specifically, according to at least one embodiment, the controller 104 analyzes the round trip time of at least one received reflection in the series of reflections and utilizes the round trip time to determine if the connection (i.e., at the terminal 106) is faulty (e.g., loose). The round trip time of the received reflection varies depending on the integrity of the connection (i.e., at the terminal 106) of the power distribution block 110. For example, in at least one embodiment, a loose connection (e.g., between a wire and the terminal 106) results in increased electrical and mechanical impedance in the power distribution block 110 and an increased round trip time. Alternatively, a tightened connection results in decreased electrical and mechanical impedance in the power distribution block 110 and a decreased round trip time.

By monitoring the round trip time of the at least one received reflection, the controller 104 can determine the integrity of the connection at the terminal 106. For example, in one embodiment, the controller 104 identifies the round trip time of the most prominent reflected pulse (i.e., the reflected pulse having the largest magnitude) received by the transducer 102 when the power distribution block 110 includes a correctly performing (i.e., an appropriately tightened) electrical connection at the terminal 106. The controller 104 then continues to analyze the round trip time of the most prominent reflected pulse received by the transducer 102 to determine if the round trip time changes. If the controller 104 recognizes variations in the measured round trip time of the most prominent reflected pulse, the controller 104 identifies that the connection at the terminal 106 is faulty. According to at least one embodiment, if the round trip time of the most prominent reflected pulse has increased, the controller 104 identifies that the impedance of the power distribution block 110 has increased and that the connection at the terminal 106 has loosened.

As described above, the single round trip time of the most prominent reflected pulse received by the transducer 102 is utilized by the controller 104 to identify whether a status of the connection at the terminal 106 has changed (e.g., loosened). In at least one embodiment, the controller 104 utilizes multiple round trip time values from multiple reflected pulses to further characterize the integrity of the connection. For example, in one embodiment, the controller 104 utilizes the round trip time of at least one secondary return pulse (i.e., a reflected pulse having a magnitude less than the most prominent reflected pulse) to further characterize the connection at the terminal 106. By utilizing multiple round trip time values corresponding to multiple reflections, the controller 104 can better characterize the mechanical properties of the connection (e.g., the actual torque characteristics of the set screw 109 in the connection). In other embodiments, any number of reflections and round trip time values can be analyzed to characterize the mechanical properties of an electrical connection.

According to one embodiment, the controller 104 is an analog front end controller. For example, in one embodiment, the controller 104 is a TDC1000 Ultrasonic Sensing Analog Front End (AFE) controller manufactured by Texas Instruments, of Dallas, Tex. However, in other embodiments, another type of controller capable of analyzing ultrasonic pulses may be utilized.

As described above, the controller 104 is configured to monitor the integrity of an electrical connection and determine whether the electrical connection has loosened. However, in at least one embodiment, the controller 104 is configured to simply monitor the status of a parameter associated with an electrical connection (e.g., the round trip time of the most prominent reflected pulse received by the transducer 102) while a different system (e.g., an external system in communication with the controller 104) analyzes the information from the controller 104 to determine if the status of the electrical connection has changed (e.g., loosened).

According to one embodiment, the controller 104 is configured to provide information regarding a monitored connection to a system 105 operated by a user. In one embodiment, the controller 104 provides measured round trip time information to the system 105 for further processing/analysis. In another embodiment, the controller 104 provides more detailed information regarding a monitored electrical connection (e.g., an identification of a specific loose connection, specific information regarding mechanical characteristics [e.g., torque] of the electrical connection, or some other information related to the integrity of the electrical connection) to the system 105. In one embodiment, the system 105 includes a display that provides information regarding a monitored electrical connection to a user via a Graphical User Interface (GUI). In one embodiment, the system 105 and the controller 104 communicate wirelessly. For example, in at least some embodiments, the system 105 and the controller 104 communicate via a radio-, acoustic-, or an optical-based interface. According to one embodiment, the transducer 102 is configured to communicate directly with a transducer in the system 105 utilizing ultrasonic pulses. In another embodiment, the system 105 and the controller 104 communicate via a serial interface. In other embodiments, the system 105 and the controller 104 communicate via another appropriate type of interface.

Figure 2A:
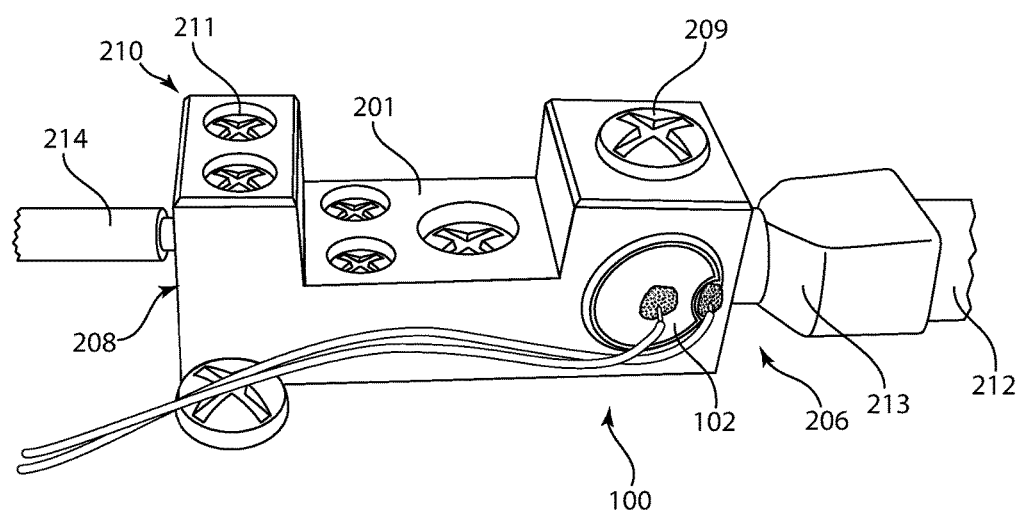
FIG. 2A is a schematic diagram of one embodiment of an electrical connection sensor in accordance with aspects of the present invention.

FIG. 2A is a schematic diagram of one embodiment of the electrical connection sensor 100 coupled to a power distribution block 210 in accordance with aspects described herein. Similarly as described above with regard to the power distribution block 110 of FIG. 1, the power distribution block 210 includes a housing 201, a terminal 206 located in the housing 201, and at least one terminal 208 located in the housing 201. The terminal 206 includes a corresponding set screw 209 and a cavity. Each terminal 208 also includes a corresponding set screw 211 and a cavity. The cavity of the terminal 206 is configured to receive a wire 212. Once a wire 212 is inserted into the cavity of the terminal 206, a user can tighten the set screw 209 to compress the wire against a contact surface in the cavity of the terminal 206. The cavity of each terminal 208 is configured to receive a wire 214. Once a wire 214 is inserted into the cavity of a terminal 208, a user can tighten the corresponding set screw 212 to compress the wire against a contact surface in the cavity of the terminal 208. When the wire 212 is coupled to the terminal 206 and the wire 214 is coupled to the terminal 208, the wire 212 is electrically coupled to the wire 214.

According to one embodiment, at least one of the wires is coupled to a terminal with a ferrule. For example, in one embodiment shown in FIG. 2A, the wire 212 is coupled to the terminal 206 with a ferrule 213; however, in other embodiments, any other wire may be coupled to a terminal with any type of ferrule or other wire-strengthening device (e.g., copper tape). In at least one other embodiment, any of the wires may be coupled to a terminal without a ferrule or wire-strengthening device.

As similarly discussed above, the transducer 102 of the electrical connection sensor 100 is coupled to the power distribution block 210 adjacent the terminal 206. In one embodiment, the transducer 102 is a piezoelectric ceramic disc transducer (such as the SMD10T2R111 10×2 mm, R, 215 KHz Piezo Electric Ceramic Disc Transducer manufactured by Steiner & Martins, Inc. of Doral, Fla.); however, in other embodiments, another appropriate transducer capable of transmitting and receiving ultrasonic pulses may be utilized). In one embodiment, the transducer 102 is secured to the power distribution block 210 with an adhesive (e.g., cyanoacrylate) adjacent the terminal 206; however, in other embodiments, any other appropriate adhesive or fastener may be utilized to couple the transducer 102 to the power distribution block 210. In one embodiment, the transducer 102 is removeably coupled to the power distribution block 210. In another embodiment, the transducer 102 is permanently secured to the power distribution block 210. As also described above, the transducer 102 is coupled to a controller (e.g., the controller 104 discussed above with respect to FIG. 1.)

In one embodiment, shown in FIG. 2A, the power distribution block 210 is a 9080LBA262104 Power Distribution Block manufactured by Schneider Electric of West Kingston, R.I.; however, in other embodiments, the electrical connection sensor 100 may be utilized with another type of power distribution block (i.e., the transducer 102 may be coupled to another type of power distribution block).

Figure 2B:
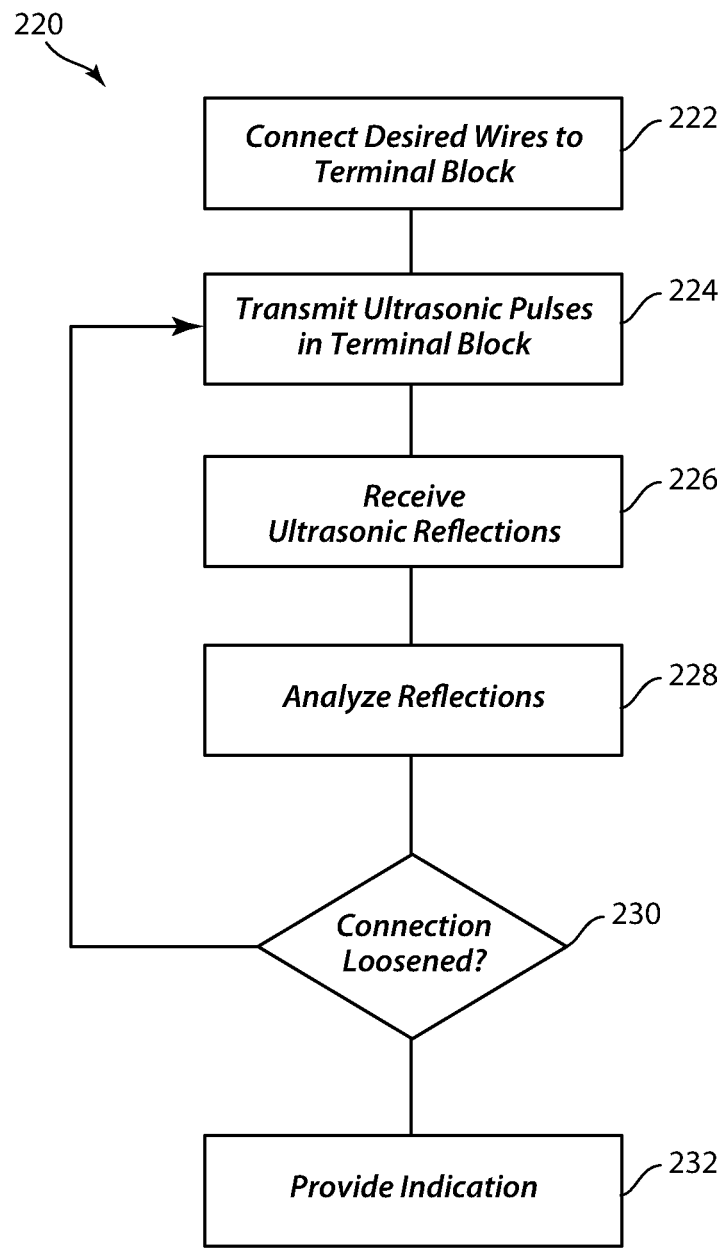
FIG. 2B is a process flow chart illustrating one embodiment of the operation of an electrical connection sensor in accordance with aspects of the present invention.

Operation of the electrical connection sensor 100 shown in FIG. 2A is discussed in greater detail below with respect to FIG. 2B. FIG. 2B is a process flow chart 220 illustrating one embodiment of the operation of the sensor 100. At block 222, the wire 212 is inserted into the cavity of the terminal 206 and the screw 209 is tightened to secure the wire 212 within the terminal 206. At block 224, the transducer 102 generates ultrasonic pulses in the power distribution block 210. The ultrasonic pulses reflect off of the boundaries and interfaces of the power distribution block 210 at the terminal 206 and, at block 226, these reflections are received by the transducer 102. At block 228, the controller 104 analyzes one or more characteristics of the reflections received by the transducer 102 to evaluate the mechanical integrity of the connection (i.e., of the wire 212 to the terminal 206) of the power distribution block 210. More specifically, according to at least one embodiment, the controller 104 analyzes the round trip time of at least one received reflection (e.g., the round trip time of the most prominent reflected pulse received by the transducer 102, as described above) and utilizes the round trip time to determine if the connection (i.e., of the wire 212 to the terminal 206) is faulty (e.g., loose). As described above, the round trip time of the received reflection varies depending on the integrity of the electrical connection between the wire 212 and the terminal 206. For example, according to at least one embodiment, as the electrical connection loosens, the mechanical and electrical impedance of the power distribution block 210 increases, resulting in an increase in round trip time of the received reflection. At block 230, based on the analysis of the received reflections, the controller 104 determines if the connection of the wire 212 to the terminal 206 has loosened. In response to a determination that the connection has not loosened (e.g., because a monitored round trip time of at least one received reflection has not changed), the transducer 102 continues to transmit and receive ultrasonic pulses and the controller 104 continues to analyze the received reflections (e.g., at blocks 224-228). In response to a determination that the connection has loosened (e.g., because a monitored round trip time of at least one received reflection has changed), the controller 104 provides an indication (e.g., to the user system 105) that the connection has loosened. By monitoring variations in the round trip time of at least one received reflection, the controller 104 can determine the integrity of the connection between the wire 212 and the terminal 206.

As shown in FIG. 2A, the transducer 102 of the electrical connection sensor 100 is coupled to the housing 201 of the power distribution block 210 such that the transducer 102 is orthogonal to the set screw 209 and in-line with the terminal 206. However, in other embodiments, the transducer 102 may be coupled to the power distribution block 210 differently. For example, in one embodiment, the transducer 102 is coupled in line with the set screw 209 and on a bottom surface of the terminal 106. Such a configuration may allow for more detailed information regarding the electrical connection to be extracted from the analysis of the reflections received by the transducer 102. For example, in one embodiment, the controller 104 may not only identify that an electrical connection has loosened (based on an identification that the round trip time of a received reflection has increased), but may also be able to specifically identify, based on received reflections, whether a corresponding set screw has been tightened correctly (i.e., is at the correct retention torque). In one embodiment, the controller 104 may be configured to determine the actual torque used to tighten the set screw. In other embodiments, the transducer 102 may be coupled to the housing 201 of the power distribution block 210 at any other appropriate location.

Figure 3:
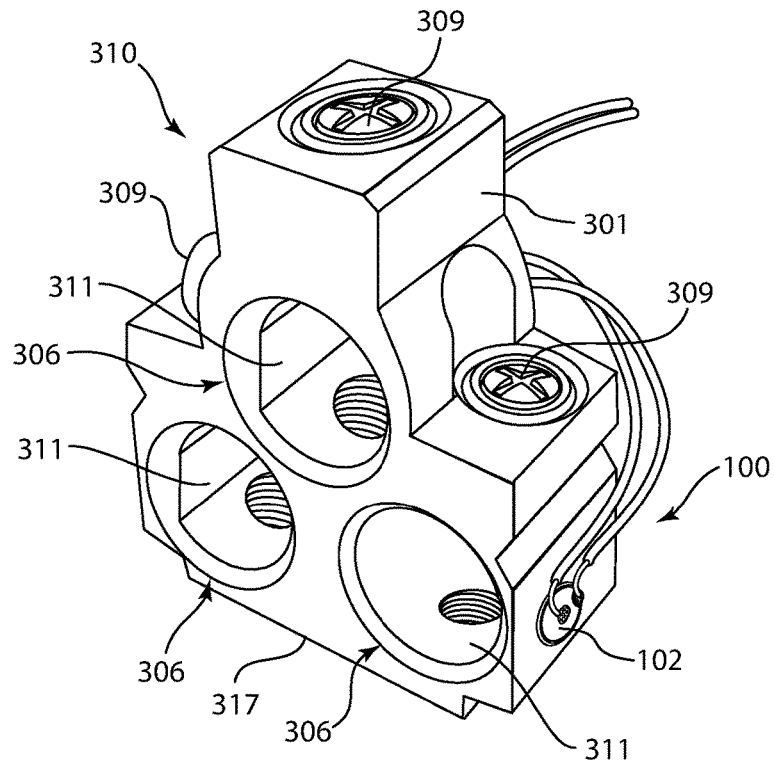
FIG. 3 is a schematic diagram of another embodiment of an electrical connection sensor in accordance with aspects of the present invention.

The electrical connection sensor 100 described above may be used with other types of power distribution blocks. For example, FIG. 3 is a schematic diagram of another embodiment of the electrical connection sensor 100 coupled to a power distribution block 310 in accordance with aspects described herein. As shown in FIG. 3, the power distribution block 310 is an AL800M23 Lug manufactured by Schneider Electric of West Kingston, R.I. The power distribution block 310 and electronic connection sensor 100 operate substantially the same as described above with regard to FIGS. 1 and 2A. More specifically, the power distribution block 310 includes a housing 301 and terminals 306 located in the housing 301. Each terminal 306 includes a corresponding set screw 309 and a cavity 311. The cavity 311 of each terminal 306 is configured to receive a wire. A bottom portion 317 of the power distribution block 310 is configured to be coupled to a bus-bar.

Once a wire is inserted into the cavity 311 of a terminal 306, a user can tighten the corresponding set screw 309 to compress the wire against a contact surface in the corresponding cavity 311 of the terminal 306. When the wire is coupled to the terminal 306, the wire is electrically coupled to the bus-bar that is coupled to bottom portion 317 of the distribution block 310. The bus-bar coupled to the bottom portion 317 of the distribution block 310 may be simultaneously coupled to a wire in any one of the terminals 306.

The transducer 102 (e.g., a piezoelectric ceramic disc transducer) of the electrical connection sensor 100 is coupled to the power distribution block 310 adjacent a terminal 306. In one embodiment, the transducer 102 is coupled to the power distribution block 310 with an appropriate adhesive or fastener. In one embodiment, the transducer 102 is removably coupled to the power distribution block 310. In another embodiment, the transducer 102 is permanently secured to the power distribution block 310. As shown in FIG. 3, the transducer 102 is coupled to the housing 301 of the power distribution block 310 such that the transducer 102 is orthogonal to a set screw 309 and in-line with a terminal 306. However, in other embodiments, the transducer 102 may be coupled to the power distribution block 310 in another appropriate way. The transducer 102 is also coupled to a controller (e.g., the controller 104 discussed above with respect to FIG. 1.)

In operation, the transducer 102 generates ultrasonic pulses in the power distribution block 310. The ultrasonic pulses reflect off of the boundaries and interfaces of the power distribution block 310 at the adjacent terminal 306 and these reflections are received by the transducer 102. The controller 104 analyzes one or more characteristics of the reflections received by the transducer 102 to evaluate the mechanical integrity of the adjacent connection (i.e., the connection at the adjacent terminals 306) of the power distribution block 310. More specifically, according to at least one embodiment, the controller 104 analyzes the round trip time of at least one received reflection (e.g., the round trip time of the most prominent reflected pulse received by the transducer 102, as described above) and utilizes the round trip time to determine if the connection (i.e., at the adjacent terminal 306) is faulty (e.g., loose). As described above, the round trip time of the received reflection varies depending on the integrity of the electrical connection between the wire and the adjacent terminal 306. For example, according to at least one embodiment, as the electrical connection loosens, the impedance of the power distribution block 310 increases, resulting in an increase in round trip time of the received reflection. By monitoring variations in the round trip time of the at least one received reflection, the controller 104 can determine the integrity of the connection at the adjacent terminal 306.

Figure 4:
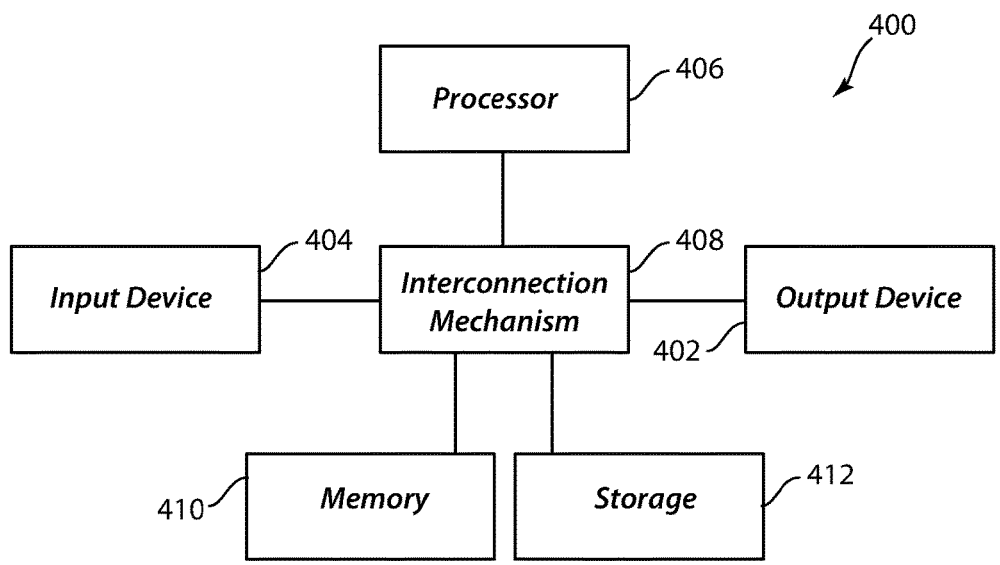
FIG. 4 is a block diagram of a system upon which various embodiments of the invention may be implemented.

FIG. 4 illustrates an example block diagram of computing components forming a system 400 which may be configured to implement one or more aspects disclosed herein. For example, the system 400 may be communicatively coupled to the controller 104, included within the controller 104, coupled to the user system 105, or included within the user system 105. The system 400 may also be configured to analyze ultrasonic reflections in a power distribution block as discussed above.

The system 400 may include for example a computing platform such as those based on Intel PENTIUM-type processor, Motorola PowerPC, Sun UltraSPARC, Texas Instruments-DSP, Hewlett-Packard PA-RISC processors, or any other type of processor. System 400 may include specially-programmed, special-purpose hardware, for example, an application-specific integrated circuit (ASIC). Various aspects of the present disclosure may be implemented as specialized software executing on the system 400 such as that shown in FIG. 4.

The system 400 may include a processor/ASIC 406 connected to one or more memory devices 410, such as a disk drive, memory, flash memory or other device for storing data. Memory 410 may be used for storing programs and data during operation of the system 400. Components of the computer system 400 may be coupled by an interconnection mechanism 408, which may include one or more buses (e.g., between components that are integrated within a same machine) and/or a network (e.g., between components that reside on separate machines). The interconnection mechanism 408 enables communications (e.g., data, instructions) to be exchanged between components of the system 400. The system 400 also includes one or more input devices 404, which may include for example, a keyboard or a touch screen. The system 400 includes one or more output devices 402, which may include for example a display. In addition, the computer system 400 may contain one or more interfaces (not shown) that may connect the computer system 400 to a communication network, in addition or as an alternative to the interconnection mechanism 408.

The system 400 may include a storage system 412, which may include a computer readable and/or writeable nonvolatile medium in which signals may be stored to provide a program to be executed by the processor or to provide information stored on or in the medium to be processed by the program. The medium may, for example, be a disk or flash memory and in some examples may include RAM or other non-volatile memory such as EEPROM. In some embodiments, the processor may cause data to be read from the nonvolatile medium into another memory 410 that allows for faster access to the information by the processor/ASIC than does the medium. This memory 410 may be a volatile, random access memory such as a dynamic random access memory (DRAM) or static memory (SRAM). It may be located in storage system 412 or in memory system 410. The processor 406 may manipulate the data within the integrated circuit memory 410 and then copy the data to the storage 412 after processing is completed. A variety of mechanisms are known for managing data movement between storage 412 and the integrated circuit memory element 410, and the disclosure is not limited thereto. The disclosure is not limited to a particular memory system 410 or a storage system 412.

The system 400 may include a computer platform that is programmable using a high-level computer programming language. The system 400 may be also implemented using specially programmed, special purpose hardware, e.g. an ASIC. The system 400 may include a processor 406, which may be a commercially available processor such as the well-known Pentium class processor available from the Intel Corporation. Many other processors are available. The processor 406 may execute an operating system which may be, for example, a Windows operating system available from the Microsoft Corporation, MAC OS System X available from Apple Computer, the Solaris Operating System available from Sun Microsystems, or UNIX and/or LINUX available from various sources. Many other operating systems may be used.

The processor and operating system together may form a computer platform for which application programs in high-level programming languages may be written. It should be understood that the disclosure is not limited to a particular computer system platform, processor, operating system, or network. Also, it should be apparent to those skilled in the art that the present disclosure is not limited to a specific programming language or computer system. Further, it should be appreciated that other appropriate programming languages and other appropriate computer systems could also be used.

As described above, the electrical connection sensor includes a single transducer; however, in other embodiments, the electrical connection sensor may include more than one transducer. For example, in one embodiment, the electrical connection sensor includes a first transducer configured to generate ultrasonic pulses in a power distribution block and monitor resulting reflections and a second transducer for monitoring the pulses generated by the first transducer. In such an embodiment, the additional information provided by the added transducer will assist the controller 104 and/or user to further defining the integrity of the connection.

As described above, the electrical connection sensor includes a transducer that is configured to transmit ultrasonic pulses in a power distribution block and monitor resulting reflections. However, in another embodiment, the electrical connection sensor may include a transducer at a first location on the power distribution block that is configured to transmit ultrasonic pulses and one or more transducers at one or more different locations of the power distribution block that are configured to receive the ultrasonic pulses from the transducer at the first location, after the ultrasonic pulses have passed through an electrical connection. By monitoring changes in the pulses received by the one or more transducers at the one or more difference locations, a controller can determine whether a status of the connection has changed.

In another embodiment, the electrical connection sensor includes a first transducer for monitoring a first connection in a power distribution block and a second transducer for monitoring a second connection in the power distribution block. In such an embodiment, the first transducer generates ultrasonic pulses adjacent the first connection and monitors reflections received from the first connection. The second transducer generates ultrasonic pulses adjacent the second connection and monitors reflections received from the second connection. In one embodiment, each transducer on the power distribution block is coupled to a separate controller which is configured to monitor information provided by the corresponding transducer. In another embodiment, each transducer on the power distribution block is coupled to the same controller, and the single controller is configured to monitor the information provided by each transducer.

As described above, the transducer of the electrical connection sensor is configured to generate pulses in the power distribution block 110 which are directed at a specific connection and the resulting reflections are analyzed with respect to the single connection. However, in other embodiments, the transducer may be located on the power distribution block in such a way (e.g., in the middle of the power distribution block) that its transmitted ultrasonic pulses (and resulting reflections) pass through multiple electrical connections. In this way, variations in the round trip time of the reflections received by the transducer may indicate whether any one of the multiple electrical connections has loosened. The electrical connection sensor may include any number of transducers, configured in any number of ways, to monitor any appropriate number of electrical connections in a power distribution block.

As described above, a controller identifies a loose connection in response to sensing an increased round trip time of a received reflection. However, in at least one other embodiment, a controller identifies a loose connection in response to sensing a decreased round trip time of a received reflection. In such an embodiment, a loose connection (e.g., between a wire and the terminal) results in decreased electrical and mechanical impedance in a power distribution block and a decreased round trip time. Alternatively, a tightened connection results in increased electrical and mechanical impedance in the power distribution block and an increased round trip time. The proportional response (i.e., either increasing or decreasing) of the round trip time of a reflection received from an electrical connection in response to the tightening or loosening of the electrical connection depends on the geometry of the power distribution block.

As described above, a controller is configured to identify a loose or overtightened connection by monitoring the round trip time of received reflections. However, according to other embodiments, the controller is configured to monitor some other characteristic of the received reflections to identify a loose or overtightened connection. For example, the controller may analyze the signal intensity and/or shape of received reflections to determine if a connection has loosened or been overtightened. A specific intensity level of a received reflection or a specific waveform shape by identify to the controller that an electrical connection is loose or has been overtightened.

As described above, the controller 104 is configured to identify the calculated round trip time of at least one received reflection when a connection is known to be correctly performing (i.e., is appropriately tightened) and to compare that round trip time to subsequent round trip time calculations to determine if the connection has loosened (e.g., based on a determination that a monitored round trip time has changed). However, in at least one other embodiment, the controller 104 is configured to compare received reflections to data previously identified in a calibration process. For example, in one embodiment, during a calibration process for a specific type of power distribution block, a user may identify a specific waveform and/or round trip time that indicates a correctly performing connection in the specific type of power distribution block. The specific waveform and/or round trip time (i.e., calibration data) are stored in the controller 104 or in corresponding memory. When the controller 104 analyzes reflections received by the transducer 102, it compares the received reflections and/or corresponding round trip times to the previously stored calibration data. If the round trip times and/or waveforms differ from the calibration data, the controller 104 identifies that a connection in the power distribution block is loose or overtightened.

As described above, according to at least one embodiment, the transducer of the electrical connection sensor is attached directly to the power distribution block 110 via an adhesive or fastener that provides electrical isolation between the transducer and the power distribution block. According to another embodiment, the transducer is attached to the power distribution block via a plastic insulator (e.g., a plastic film). This electrically isolates the transducer from the power distribution block while also providing a calibration point for reference. For example, the reflection from the insulator-power distribution block boundary can be used to calibrate the electrical connection sensor if the insulator's thickness and composition is fixed. According to other embodiments, another type of device that electrically isolates the transducer from the power distribution block may be utilized.

According to one embodiment, the electrical connection sensor described above is utilized to monitor at least one electrified connection; however, in other embodiments, the electrical connection sensor can be utilized to monitor at least one non-electrified terminal or connection (e.g., screws).

As discussed above, the electrical connection sensor can be utilized with a power distribution block. In at least one other embodiment, the electrical connection sensor is integrated into a test jig which is calibrated for a particular product or production assembly that includes screw type connections (that are used for electrical connections or simply mechanical securement). A technician could characterize the pulse response from a correctly assembled sample, and thereafter compare the pulse response from a correctly assembled sample to the pulse response of other tested samples. A variation in pulse responses would indicate that the tested product was not assembled correctly. This could reduce the cost of failures which may occur due to the difficulty of maintaining exact torque levels in product manufacturing. In other embodiments, the electrical connection sensor can be utilized with any other apparatus including at least one electrical connection that requires monitoring.

As described above, a more efficient, cost-effective, and accurate electrical connection sensor for the continuous monitoring of the mechanical state of an electrical connection is provided. The sensor includes a transducer that probes the mechanical interface between set screw, cable, and housing using ultrasonic pulses. The sensor analyzes one or more characteristics (e.g., round trip time, intensity, shape, etc.) of resulting reflections to determine the state of at least one electrical connection. For example, in one embodiment, an analog electronic front end measures the round trip time of at least one reflection received by the transducer and analyzes the round trip time to ascertain the mechanical state of the connection. By monitoring variations in the round trip time of the at least one received reflection, the analog electronic front end can accurately determine the integrity of the electrical connection while maintaining electrical isolation between the electrical connection sensor and the monitored connection and without requiring a technician to access the electrical connection.

For example, in at least one embodiment, the electrical connection sensor described herein is capable of accurately detecting a loose electrical connection that is causing a 10μΩ increase in connection resistance. Such a small increase in resistance would not generate enough heating to be detected by a common thermal imaging survey.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An electrical connection sensor comprising:
at least one transducer configured to be coupled to a power distribution block, to generate ultrasonic pulses in the power distribution block, and to receive ultrasonic signals based on the ultrasonic pulses; and
a controller coupled to the at least one transducer and configured to determine a status of at least one electrical connection in the power distribution block based on at least one characteristic of the ultrasonic signals received by the at least one transducer,
wherein the ultrasonic signals received by the at least one transducer include a series of reflections from the at least one electrical connection in the power distribution block, and
wherein in determining the status of the at least one electrical connection, the controller is further configured to determine a round trip time of at least one of the series of reflections and determine the status of the at least one electrical connection based on the round trip time of the at least one of the series of reflections.

2. The electrical connection sensor of claim 1, wherein in determining the round trip time of the at least one of the series of reflections, the controller is further configured to determine a round trip time of a most prominent reflection in the series of reflections.

3. The electrical connection sensor of claim 2, wherein in determining the status of the at least one electrical connection, the controller is further configured to analyze the round trip time of the most prominent reflection in the series of reflections over time and determine the status of the at least one electrical connection based on variations in the round trip time of the most prominent reflection in the series of reflections.

4. The electrical connection sensor of claim 3, wherein in determining the status of the at least one electrical connection, the controller is further configured to identify that the at least one electrical connection has loosened or been overtightened in response to determining that the round trip time of the most prominent reflection in the series of reflections has increased.

5. The electrical connection sensor of claim 4, wherein the controller is further configured to provide an indication to an external system that the at least one electrical connection has loosened or been overtightened.

6. The electrical connection sensor of claim 2, wherein in determining the round trip time of the at least one of the series of reflections, the controller is further configured to determine the round trip time of at least one secondary reflection in the series of reflections, and wherein in determining the status of the at least one electrical connection, the controller is further configured to determine the status of the at least one electrical connection based on the most prominent reflection and the at least one secondary reflection in the series of reflections.

7. The electrical connection sensor of claim 6, wherein in determining the status of the at least one electrical connection based on the most prominent reflection and the at least one secondary reflection in the series of reflections, the controller is further configured to identify a torque characteristic of the at least one connection based on the most prominent reflection and the at least one secondary reflection in the series of reflections.

8. The electrical connection sensor of claim 1, wherein the at least one transducer is further configured to receive the series of reflections from a first electrical connection and a second electrical connection in the power distribution block, and wherein the controller is further configured to determine a status of the first electrical connection and a status of the second electrical connection based on the round-trip time of the at least one of the series of reflections.

9. The electrical connection sensor of claim 8, wherein the at least one transducer includes a first transducer configured to receive a first series of reflections from the first electrical connection and a second transducer configured to receive a second series of reflections from the second electrical connection, and
wherein the controller is further configured to determine a first round-trip time of the first series of reflections, to determine a second round-trip time of the second series of reflections, to determine a status of the first electrical connection based on the first round-trip time, and to determine a status of the second electrical connection based on the second round-trip time.

10. The electrical connection sensor of claim 1, wherein the at least one transducer includes a first transducer configured to generate the ultrasonic pulses in the power distribution block and monitor the series of reflections received from the at least one electrical connection in the power distribution block and at least one second transducer configured to monitor the ultrasonic pulses generated by the first transducer, and
wherein the controller is further configured to determine the round-trip time of at least one of the series of reflections based on series of reflections monitored by the first transducer and the ultrasonic pulses monitored by the at least one second transducer.

11. The electrical connection sensor of claim 1, wherein the at least one transducer is configured to be coupled to the power distribution block with one of an adhesive, a magnet, and a fastener.

12. The electrical connection sensor of claim 1, wherein the at least one transducer is configured to be coupled to one of a portion of the power distribution block that is orthogonal to a set screw of the at least one electrical connection and a portion of the power distribution block that is in line with a set screw of the at least one electrical connection.

13. The electrical connection sensor of claim 1, wherein the controller is an analog front end controller.

14. A method for monitoring at least one electrical connection in a power distribution block, the method comprising:
generating, with at least one transducer, ultrasonic pulses in the power distribution block;
receiving, with the at least one transducer, ultrasonic signals based on the ultrasonic pulses; and determining, with a controller coupled to the at least one transducer, a status of at least one electrical connection in the power distribution block based on at least one characteristic of the ultrasonic signals received by the at least one transducer, wherein receiving the ultrasonic signals includes receiving, with the at least one transducer, a series of reflections from the at least one electrical connection in the power distribution block; and wherein determining the status of the at least one electrical connection includes determining a round-trip time of at least one of the series of reflections and identifying whether the at least one electrical connection in the power distribution block has loosened or been overtightened based on the round-trip time of the at least one of the series of reflections.

15. The method of claim 14, wherein determining the round-trip time of the at least one of the series of reflections includes determining a round-trip time of a most prominent reflection in the series of reflections, and wherein identifying includes analyzing the round-trip time of the most prominent reflection in the series of reflections over time and identifying that the at least one electrical connection in the power distribution block has loosened or been overtightened in response to a determination that the round-trip time of the most prominent reflection in the series of reflections has increased.

16. The method of claim 15, further comprising, in response to identifying that the at least one electrical connection has loosened or been overtightened, providing an indication to a user that the at least one electrical connection in the terminal has loosened or been overtightened.

17. The method of claim 15, further comprising:

analyzing at least one secondary reflection in the series of reflections, and determining a torque characteristic of the at least one electrical connection based on the most prominent reflection and the at least one secondary reflection.

18. A power distribution block comprising:

a housing;

at least one terminal in the housing that is configured to be coupled to a wire;

at least one transducer coupled to the housing and configured to generate ultrasonic pulses in the power distribution block and receive a series of ultrasonic signals based on the ultrasonic pulses; and a controller coupled to the at least one transducer and configured to determine a status of a connection between the wire and the at least one terminal based on at least a round-trip time of at least one of the series of the ultrasonic signals received by the at least one transducer.

* * * * *